US010393920B2

(12) United States Patent
McQuown

(10) Patent No.: US 10,393,920 B2
(45) Date of Patent: Aug. 27, 2019

(54) ASSESSING ORGANIC RICHNESS USING MICRORESISTIVITY IMAGES AND ACOUSTIC VELOCITY

(71) Applicant: Weatherford Technology Holdings, LLC, Houston, TX (US)

(72) Inventor: M. Scott McQuown, Denver, CO (US)

(73) Assignee: Weatherford Technology Holdings, LLC, Houston, TX (US)

( * ) Notice: Subject to any disclaimer, the term of this patent is extended or adjusted under 35 U.S.C. 154(b) by 0 days.

(21) Appl. No.: 15/632,971

(22) Filed: Jun. 26, 2017

(65) Prior Publication Data
US 2018/0372687 A1    Dec. 27, 2018

(51) Int. Cl.
| G01V 11/00 | (2006.01) |
| G01N 29/06 | (2006.01) |
| E21B 47/12 | (2012.01) |
| G01N 29/44 | (2006.01) |
| G01V 3/18 | (2006.01) |
| G01V 3/20 | (2006.01) |
| G01N 33/24 | (2006.01) |
| E21B 49/00 | (2006.01) |
| G01V 3/00 | (2006.01) |

(52) U.S. Cl.
CPC ............ *G01V 11/00* (2013.01); *E21B 47/122* (2013.01); *G01N 29/06* (2013.01); *G01N 29/44* (2013.01); *G01N 33/241* (2013.01); *G01V 3/18* (2013.01); *G01V 3/20* (2013.01); *E21B 49/00* (2013.01); *G01V 3/00* (2013.01); *G01V 2210/61* (2013.01); *G01V 2210/6161* (2013.01)

(58) Field of Classification Search
CPC .............. G01V 11/00; G01V 2210/61; G01V 2210/6161; G01V 2210/6163; G01N 33/24
See application file for complete search history.

(56) References Cited

U.S. PATENT DOCUMENTS

| 5,502,686 A | * | 3/1996 | Dory ...................... G01V 11/00 175/40 |
| 6,470,274 B1 | | 10/2002 | Mollison et al. |

(Continued)

FOREIGN PATENT DOCUMENTS

WO     2016/130945 A1     8/2016

OTHER PUBLICATIONS

Bailley, Treasure, et al., "Using Micro-Resistivity Imaging and Elemental Analysis Data to Identify Thin Organic-Rich Beds in the Williston Basin, North Dakota," Society of Petrophysicists and Well Log Analysis 56th Annual Logging Symposium, Jul. 2015, 8 pages.

(Continued)

*Primary Examiner* — Walter L Lindsay, Jr.
*Assistant Examiner* — Milton Gonzalez
(74) *Attorney, Agent, or Firm* — Lewis & Reese, PLLC

(57) ABSTRACT

A method for determining organic richness of a formation is disclosed. The method involves obtaining a microresistivity image of the formation, obtaining acoustic logging data for the formation, fusing the microresistivity image with the acoustic logging data to generate a fused pseudo-acoustic image of the formation, and determining an organic richness image based on the fused pseudo-acoustic image. The difference between the fused pseudo-acoustic image and the microresistivity image indicates organic richness.

17 Claims, 4 Drawing Sheets

(56) References Cited

U.S. PATENT DOCUMENTS

| | | | |
|---|---|---|---|
| 6,493,632 B1 | 12/2002 | Mollison et al. | |
| 2008/0179509 A1* | 7/2008 | Jacobi | G01V 5/104 |
| | | | 250/269.2 |
| 2011/0089950 A1 | 4/2011 | Wang | |
| 2011/0144913 A1 | 6/2011 | Klein et al. | |
| 2012/0143508 A1 | 6/2012 | Klein et al. | |
| 2012/0312090 A1 | 12/2012 | Klein et al. | |
| 2013/0234717 A1 | 9/2013 | Wang | |
| 2016/0139293 A1 | 5/2016 | Misra et al. | |
| 2016/0186556 A1 | 6/2016 | Rasmus et al. | |
| 2017/0138872 A1 | 5/2017 | Suarez-Rivera et al. | |

OTHER PUBLICATIONS

Beitz, Madeline K., et al., "Utilizing the Delta Log R Method for Determining Total Organic Carbon of the Niobrara Formation, B Bench, Denver-Julesburg Basin, Colorado and Wyoming," Search and Discovery Article, #10532, Oct. 21, 2013, 37 pages.

"Compact Formation Evaluation Services," Weatherford, 2009, 45 pages.

"Compact Microimager—Unprecedented Logging Detail and Precision with Industry-Leading Versatility," Weatherford, 2013, 4 pages.

Mirkes, Evgeny M., et al., "Psuedo-Outcrop Visualization of Borehole Images and Core Scans," Feb. 8, 2017, 18 pages.

"OBMI—Borehole Imaging in Oil-Base Mud," Schlumberger, Jul. 2006, 7 pages.

Passey, Q. R., et al., "A Practical Model for Organic Richness from Porosity and Resistivity Logs." The American Association of Petroleum Geologists Bulletin, V. 74, No. 12, Dec. 1990, pp. 1777-1794.

"SineWave Microimager," Weatherford, 2013, 3 pages.

Sun, S. Z., et al., "Methods of Calculating Total Organic Carbon from Well Logs and its Application on Rock's Properties Analysis," GeoConvention: Integration, 2013, 7 pages.

* cited by examiner

ASSESSING ORGANIC RICHNESS USING MICRORESISTIVITY IMAGES AND ACOUSTIC VELOCITY

FIELD OF THE INVENTION

The present application relates to formation evaluation, and more particularly, to methods and systems for determining organic richness.

BACKGROUND

Extracting hydrocarbons, like oil and gas, from geologic formations within the earth is an expensive operation. Before committing the required substantial costs necessary to extract hydrocarbons from a given formation, an operator must evaluate the potential of the formation to produce hydrocarbons. In other words, the operator wants to know how much hydrocarbon they may recover and how difficult will it be to recover it.

Source rock is rock that is rich in organic matter which, if heated sufficiently, will generate oil or gas. Typical source rocks, usually shales or limestones, contain about 1% organic matter and at least 0.5% total organic carbon (TOC), although a rich source rock might have as much as 10% organic matter. Clearly, an operator would like to know the amount of organic matter, or the "organic richness" of the rock in a formation to evaluate whether to commit the resources necessary to recover the rock.

Accurately quantifying organic richness of source rock is difficult. The properties and concentrations in source rocks can vary at small vertical intervals (tenths of millimeters). Evaluation therefore requires high measurement and sample resolution. Typically, assessment requires recovering rock samples and performing laboratory analysis on them to determine parameters such as TOC, mineralogy, vitrinite reflectance and ratios of carbon/oxygen and carbon/hydrogen.

It would be easier and less expensive to assess organic richness without physically recovering the rock by using standard well logging techniques, such as density, neutron, gamma ray, acoustic, and/or formation resistivity. However, those techniques lack the resolution necessary to yield meaningful information in many situations.

It has previously been shown that overlaying a properly scaled sonic transit time log on a resistivity curve (determined from a deep-reading resistivity logging tool) can yield information relating to organic richness. That technique, referred to as Δ log R technique, was described by Passey et al., (*A Practical Model for Organic Richness from Porosity and Resistivity Logs*, Am. Ass. Petr. Geo. Bull., V. 74, No. 12, 1990, 1777-94). In water-saturated, organic-lean rocks, the resistivity log and the porosity log parallel each other because both measurements respond similarly to variations in formation porosity. In organic-rich rock, the resistivity log and the porosity log respond opposite to each other, yielding a divergence between the overlaid logs. The divergence between the porosity log and the resistivity log can thus be used to indicate organic-rich formations.

While the Passey Δ log R technique provides some information relating to the organic richness of formation rock, the technique lacks spatial resolution because the resistivity log is collected at a single depth point, which depending on the sample rate and bed thickness can result in an averaging affect combining thin adjacent contrasting beds. Thus, there remains a need for higher-resolution and oriented logging techniques capable of characterizing the detailed distribution of organic matter and orientation of source rock formations and other unconventional hydrocarbon plays.

SUMMARY

The present disclosure provides methods for characterizing the detailed distribution of organic matter and orientation of source rock formations and other unconventional hydrocarbon plays. The method comprises obtaining a microresistivity image of the formation, obtaining acoustic logging data for the formation, fusing the microresistivity image with the acoustic logging data to generate a fused pseudo-acoustic image of the formation, and determining an organic richness image based on the fused pseudo-acoustic image. The fused pseudo-acoustic image of the formation is essentially a transformation of the microresistivity image based on the acoustic logging data. The difference between the fused pseudo-acoustic image and the microresistivity image indicates organic richness.

DESCRIPTION

Figure 1:
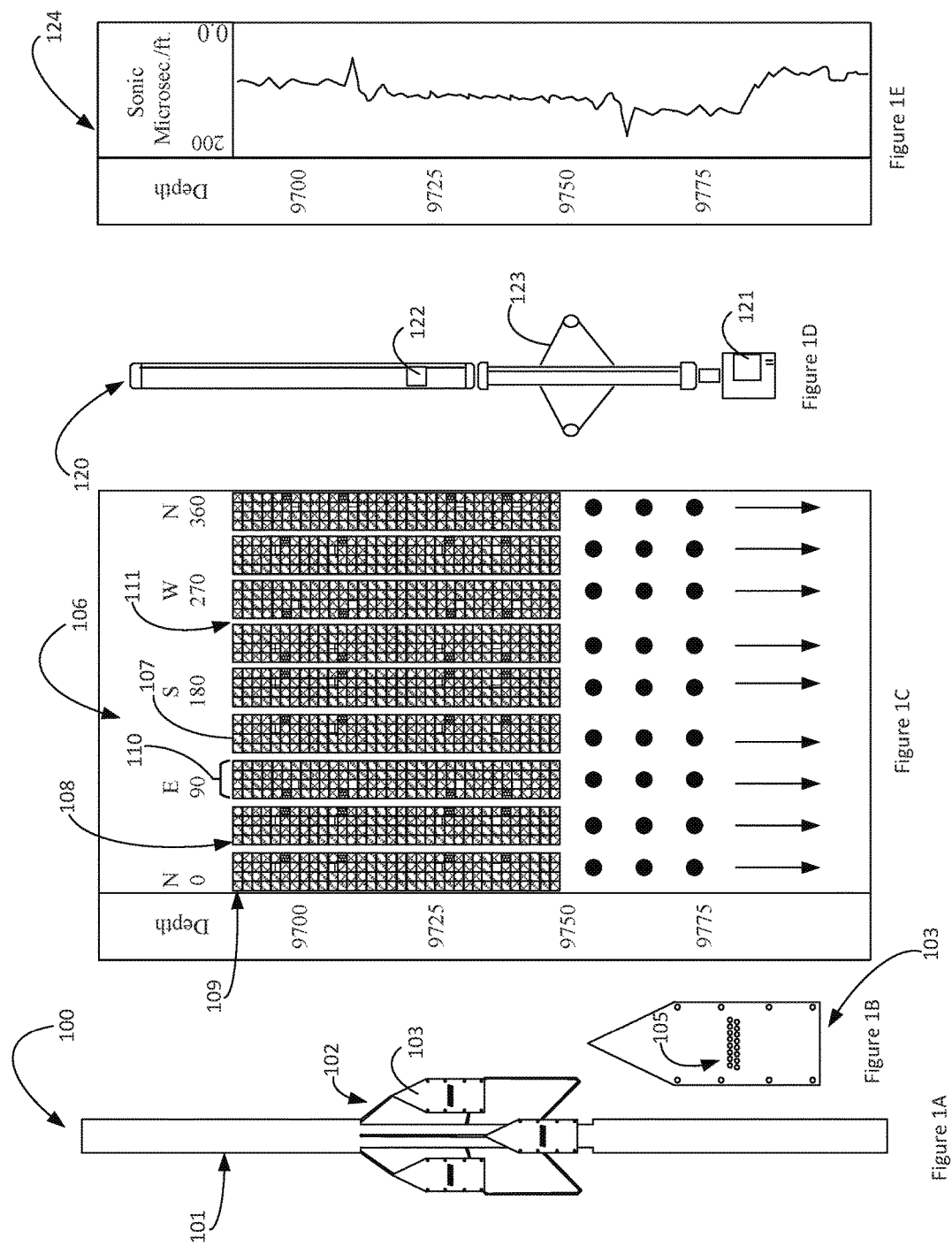
FIGS. 1A-1E illustrate tools and measurements for determining microresistivity and acoustic velocity.

FIGS. 1A-1E illustrate two types of well logging tools that operators routinely use to evaluate formations, FIG. 1A illustrates a microresistivity logging tool 100. The microresistivity logging tool 100 comprises one or more electronics sections 101 and a sonde section 102. The electronics section 101 is generally tubular and contains the electronic components to operate the tool 100, to store data that the tool records, and to communicate data and instructions between the tool and the surface of the earth. Such electronics are familiar to a person of skill in the art and are not discussed in this disclosure. The microresistivity logging tool 100 is lowered into a wellbore using a wireline that provides conveyance, electrical power, and data communication between the tool and the earth's surface. Also included in the sonde are triaxial magnetometers and accelerometers to record the tool orientation (magnetic azimuth and tool inclination). These data are used to accurately determine the orientation of geologic features. Wireline or drillpipe deployment of logging tools is familiar to persons of skill in the art. In addition, the proposed techniques can also be applied to other borehole imaging methods such as those acquired by logging while drilling (LWD) techniques.

The sonde section 102 comprises a plurality of measurement pads 103 arranged around the circumference of the microresistivity logging tool 100. For example, a microresistivity logging tool may include six measurement pads 103 to provide 360° measurements within a wellbore. The measurement pads 103 containing multiple electrodes (buttons) are attached to the microresistivity logging tool 100 via expanding caliper arms 102. When the microresistivity, logging tool 100 is deployed into a wellbore, the measurement pads 103 expand to contact the wall of the wellbore.

Thus, the microresistivity logging tool 100 may be used within wellbores having different diameters.

Referring to FIG. 1B, each measurement pad 103 includes a plurality of buttons 105 arranged in a row across the measurement pad. Resistivity is calculated at each button from the current and associated voltage drop between individual buttons and return electrode to provide a 360° microresistivity image about the circumference of the wellbore. FIG. 1C illustrates a microresistivity image 106 at various depths within a wellbore. The image 106 comprises a plurality of pixels 107 arranged as a plurality of columns 108 and rows 109. Each pixel 107 represents a sampled resistivity value between a pair of buttons 105. The color of each pixel 107 may represent the resistivity values corresponding to that location within the wellbore. For example, high resistivity values may be represented by colors toward the yellow end of the color pallet and low resistivity values may be represented by colors toward the brown end of the color pallet. Each row 109 of pixels is a plurality of resistivity measurements around the circumference of the wellbore at a particular depth within the wellbore. The columns 108 of pixels are arranged in groups 110 of columns. Each group 110 represents the resistivity measurements of the button pairs 105 on a single measurement pads 103. Depending on the diameter of the wellbore, there may be gaps between the pads 103 which are not measured. Those unmeasured gaps are represented by the gaps 111 between the groups of columns 110.

FIG. 1D shows an acoustic logging tool 120. The acoustic logging tool comprises an acoustic transmitter 121, such as a piezoelectric transducer, capable of generating an acoustic signal and one or more receivers 122 capable of detecting the acoustic signal. The acoustic logging tool can determine the time it takes the acoustic signal to travel from the transmitter to the receiver through the borehole and the adjacent rock formations. The travel time is affected by the material and structure of the formation. The acoustic logging tool 120 may include a centralizer structure 123 for keeping the tool centralized within the center of the borehole. FIG. 1E illustrates a typical acoustic log 124. Acoustic logging data is commonly expressed as "slowness," that is, the time it takes the acoustic signal to travel a unit distance through the formation, commonly expressed in microseconds/ft.

Figure 2:
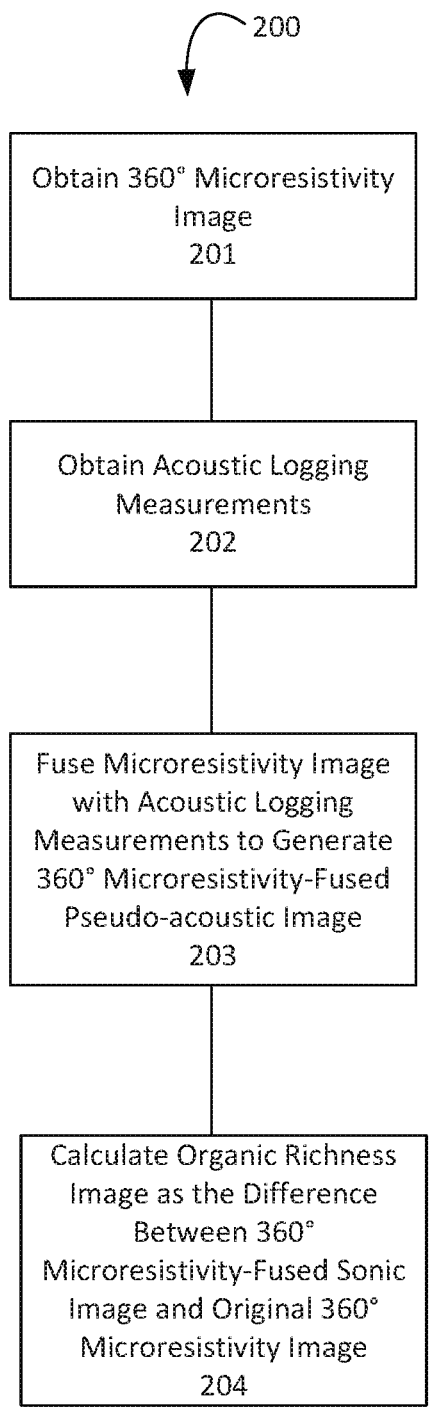
FIG. 2 shows a method of determining organic richness based on a combination microresistivity and acoustic velocity.

The inventor has discovered that integrating 360° circumferential microresistivity images, such as 106 illustrated in FIG. 1C with acoustic logging data, such as data 124 illustrated in FIG. 1E, provides high spatial resolution images correlated to organic richness. FIG. 2 illustrates a method 200 in accordance with that discovery. High resolution microresistivity images and acoustic logging measurements (both as described above) are obtained (Steps 201 and 202, respectively). The microresistivity image is then "fused" with the acoustic logging data to generate a fused "pseudo-acoustic image" 203.

Figure 3:
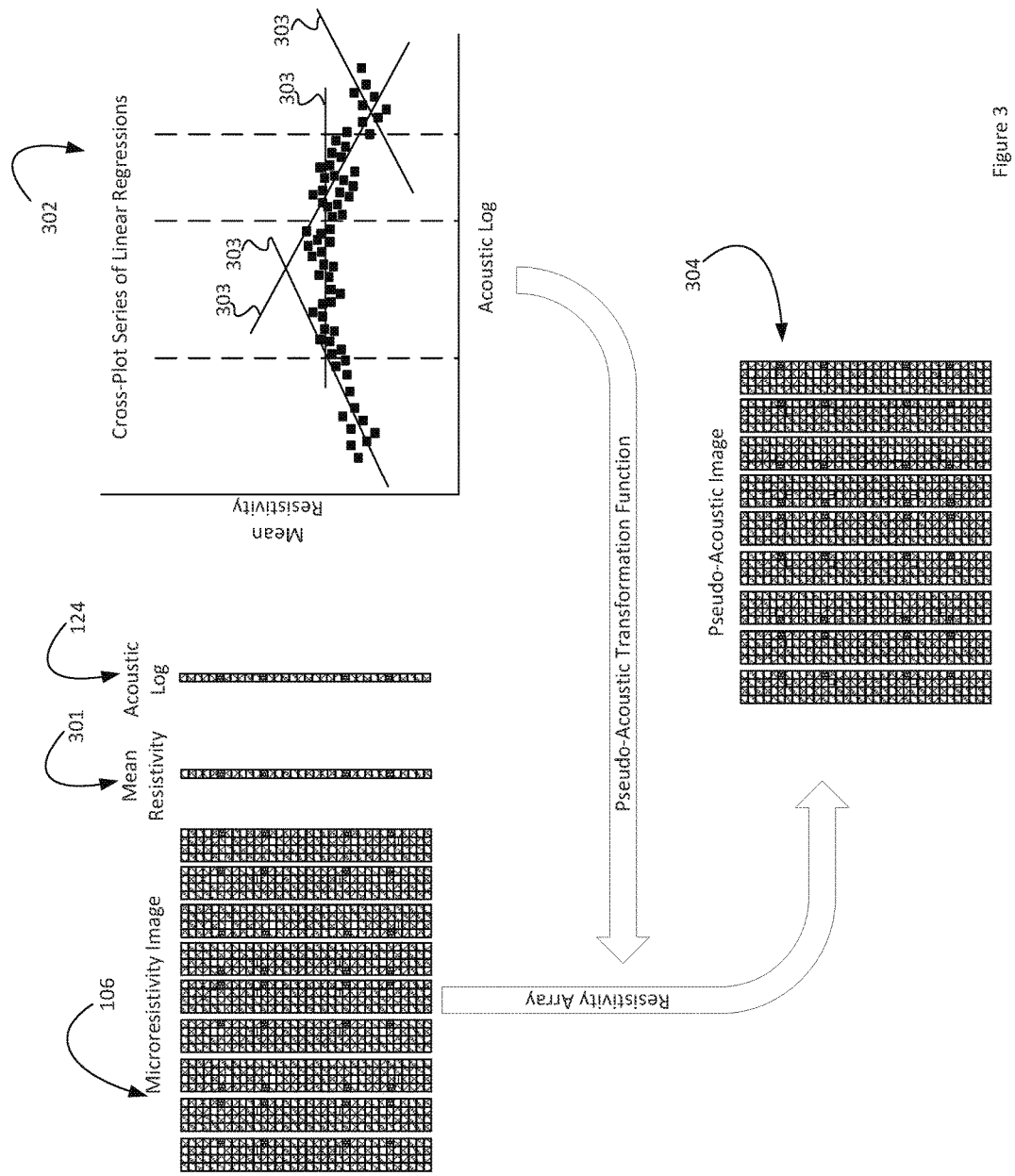
FIG. 3 shows a method of transforming a microresistivity image to generate a pseudo-acoustic image.

One method of fusing the microresistivity image with the acoustic logging data is illustrated in FIG. 3. First, a mean resistivity 301 value is calculated for each depth (i.e., for each row 109 of pixels in image 106, FIG. 1B) based on the sampled resistivities at that depth. The mean resistivity is cross-plotted against the acoustic logging data 124. The cross-plot 302 is divided into segments through which best-fit lines 303 are calculated. The barycenter of each segment is calculated and joined to produce a series of linear regressions, referred to herein as a pseudo-acoustic transformation function. The resulting pseudo-acoustic transformation function is then applied to the microresistivity image 106 to create a pseudo-acoustic image 304.

Figure 4:
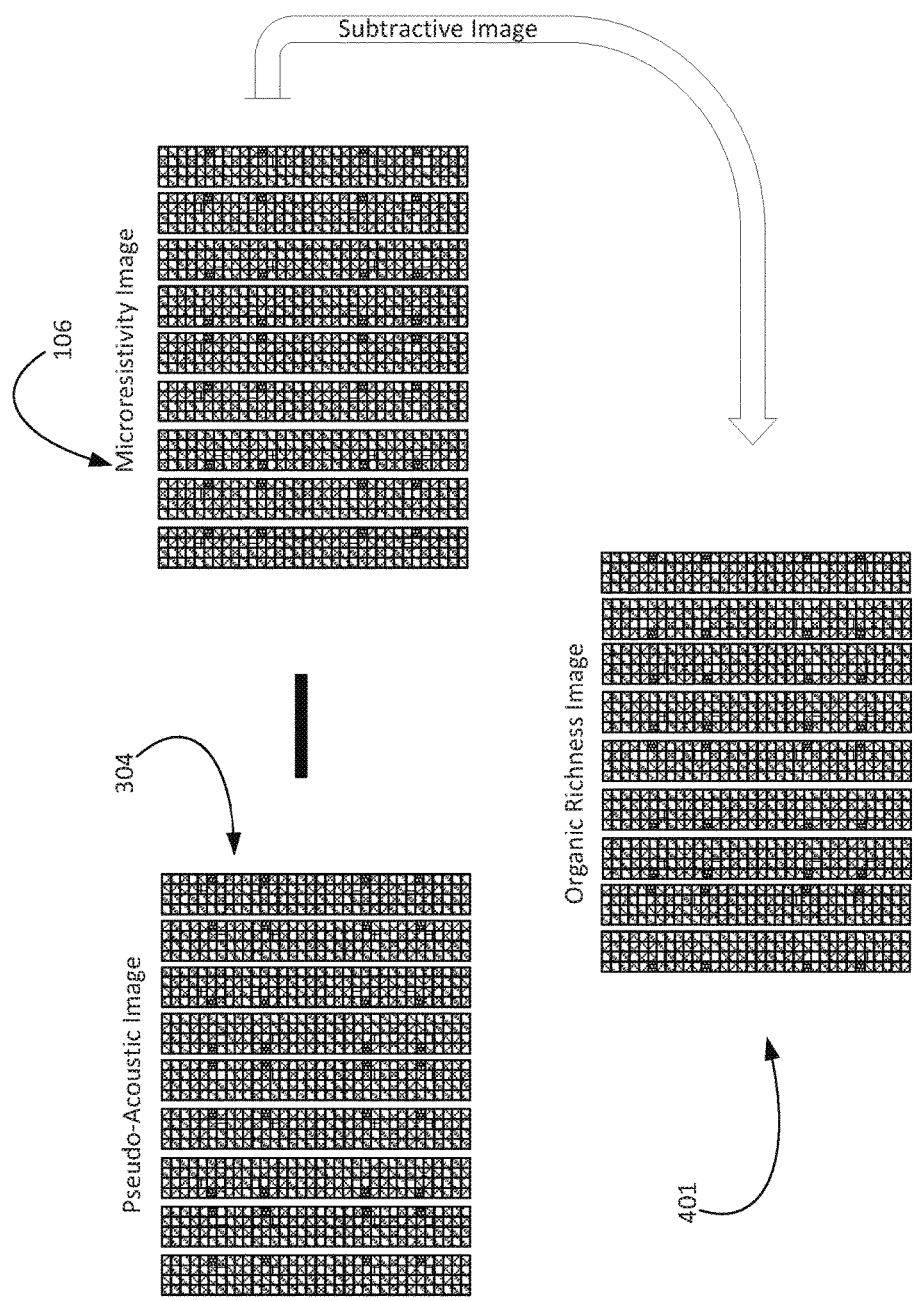
FIG. 4 shows the creation of an organic richness image.

Referring to FIGS. 2 and 4 calculating a difference 204 between the original microresistivity image 106 and the pseudo-acoustic image 304 yields an organic richness image 401 indicative of organic richness at each measured position within the wellbore. FIG. 4 schematically represents the difference calculation. The organic richness image 401 is a high resolution, 360° image indicating the degree of overlap/divergence between the resistivity and acoustic slowness within the formation. The degree of overlap or divergence can be represented by differing colors selected from a color pallet. Areas having a high degree of divergence within the organic richness image 401 indicate an area of high organic richness.

The organic richness image 401 offers several advantages over the well log-derived organic richness determination techniques described in the Background section. The organic richness image 401 provides much higher resolution, resulting in more accurate quantification of layer thicknesses. The 360° circumferential image enables determination of lateral and/or anisotropic variations in the formation layers. Since the images are oriented, layer geometry can be visualized.

Additionally, the instructions for carrying out methods described herein can be first formulated and stored as instructions in a computer-readable media, such as in a magnetic or solid state memory. The computer-readable media with such stored instructions may also comprise a device readable by the computer, such as in a memory stick or a removable disk, and may reside elsewhere. For example, the computer-readable media may be associated with a server or any other computer device, thus allowing instructions to be downloaded to the a computer via the Internet for example.

While the invention herein disclosed has been described in terms of specific embodiments and applications thereof, numerous modifications and variations could be made thereto by those skilled in the art without departing from the scope of the invention set forth in the claims.

What is claimed is:

1. A method of determining organic richness in a formation, the method comprising:
   obtaining a microresistivity image of a wellbore penetrating the formation, wherein the microresistivity image comprises a two-dimensional image indicating microresistivity values around a circumference of the wellbore at a plurality of locations within the wellbore;
   obtaining acoustic logging data for the formation;
   fusing the microresistivity image with the acoustic logging data to generate a pseudo-acoustic image of the formation, wherein fusing the microresistivity image with the acoustic logging data comprises:
      determining a microresistivity value at each of the plurality of locations within the wellbore,
      using a series of linear regressions to correlate the microresistivity values to the acoustic logging data to generate a pseudo-acoustic transformation function, and
      transforming the microresistivity image using the pseudo-acoustic transformation function to generate the pseudo-acoustic image; and
   determining an organic richness image based on the pseudo-acoustic image.

2. The method of claim 1, further comprising using a plurality of electrodes disposed around the circumference of the wellbore to determine the microresistivity values.

3. The method of claim 2, wherein the microresistivity values are correlated to an orientation of the plurality of electrodes.

4. The method of claim 1, wherein the acoustic logging data comprises acoustic travel times determined at the plurality of locations within the wellbore.

5. The method of claim 1, wherein determining an organic richness image comprises determining a difference between the pseudo-acoustic image and the microresistivity image, wherein the difference indicates organic richness.

6. The method of claim 1, wherein determining an organic richness image comprises determining a difference between the pseudo-acoustic image and the acoustic log, wherein the difference indicates organic richness.

7. The method of claim 1, wherein the formation comprises source rock.

8. A non-transitory computer-readable media comprising non-transitory instructions for execution by a computer processor, wherein the instructions are configured to cause the computer processor to:
   obtain a microresistivity image of a wellbore penetrating a formation, wherein the microresistivity image comprises a two-dimensional image indicating microresistivity values around a circumference of the wellbore at a plurality of locations within the wellbore;
   obtain acoustic logging data for the formation;
   fuse the microresistivity image with the acoustic logging data to generate a pseudo-acoustic image of the formation, wherein fusing the microresistivity image with the acoustic logging data comprises:
      determining a microresistivity value at each of the plurality of locations within the wellbore,
      using a series of linear regressions to correlate the microresistivity values to the acoustic logging data to generate a pseudo-acoustic transformation function, and
      transforming the microresistivity image using the pseudo-acoustic transformation function to generate the pseudo-acoustic image; and
   determine an organic richness image based on the pseudo-acoustic image.

9. The non-transitory computer-readable media of claim 8, wherein the microresistivity image is stored in a storage and wherein the plurality of microresistivity values are determined at a plurality of electrodes disposed around the circumference of the wellbore.

10. The non-transitory computer-readable media of claim 9, wherein the microresistivity values are correlated to an orientation of the plurality of electrodes.

11. The non-transitory computer-readable media of claim 8, wherein the acoustic logging data is stored in a storage and comprises acoustic travel times determined at the plurality of locations within the wellbore.

12. The non-transitory computer-readable media of claim 8, wherein determining an organic richness image comprises determining a difference between the pseudo-acoustic image and the microresistivity image, wherein the difference indicates organic richness.

13. The non-transitory computer-readable media of claim 8, wherein determining an organic richness image comprises determining a difference between the pseudo-acoustic image and the acoustic log, wherein the difference indicates organic richness.

14. The non-transitory computer-readable media of claim 8, wherein the formation comprises source rock.

15. A method of determining organic richness in a formation, the method comprising:
   obtaining a microresistivity image of a wellbore penetrating the formation, wherein the microresistivity image comprises a two-dimensional array of pixels indicating microresistivity values around a circumference of the wellbore at a plurality of locations within the wellbore,
   obtaining acoustic logging data for the formation,
   correlating the acoustic logging data with the microresistivity image, and
   determining for each pixel of the microresistivity image a divergence between the acoustic logging data and the microresistivity values, wherein the divergence indicates organic richness, wherein
   correlating the acoustic logging data with the microresistivity image comprises:
      determining a microresistivity value at each of the plurality of locations within the wellbore,
      using a series of linear regressions to correlate the microresistivity values to the acoustic logging data to generate a pseudo-acoustic transformation function, and
      transforming the microresistivity image using the pseudo-acoustic transformation function to generate a pseudo-acoustic image.

16. The method of claim 15, wherein determining a divergence between the acoustic logging data and the microresistivity values comprises determining a difference between the pseudo-acoustic image and the microresistivity image.

17. The method of claim 15, wherein determining a divergence between the acoustic logging data and the microresistivity values comprises determining a difference between the pseudo-acoustic image and the acoustic log.

* * * * *